United States Patent [19]

Mulder

[11] Patent Number: 5,565,189
[45] Date of Patent: Oct. 15, 1996

[54] WOUND CLEANSER METHOD OF USE

[76] Inventor: Gerit D. Mulder, 4850 S. Lafayette La., Englewood, Colo. 80110

[21] Appl. No.: 383,508

[22] Filed: Feb. 3, 1995

[51] Int. Cl.$^6$ ..................................................... A61K 9/10
[52] U.S. Cl. ...................................... 424/43; 424/DIG. 13
[58] Field of Search ............................ 424/400, DIG. 13, 424/43; 604/289, 310, 311

[56] References Cited

U.S. PATENT DOCUMENTS

| | | | |
|---|---|---|---|
| 3,103,466 | 9/1963 | Farkas | 514/54 |
| 4,593,046 | 6/1986 | Gruber | 514/717 |
| 4,748,022 | 5/1988 | Busciglio | 424/195.1 |
| 5,078,991 | 1/1992 | Birtwistle et al. | 424/70.23 |
| 5,110,593 | 5/1992 | Benford | 424/401 |
| 5,378,465 | 1/1995 | Zeines | 424/195.1 |

OTHER PUBLICATIONS

Cosmetic Ingredient Review; Ingredient Publication Status; Jun. 24, 1994; pp. 1–24.

*Primary Examiner*—John C. Bleutge
*Assistant Examiner*—Robert H. Harrison
*Attorney, Agent, or Firm*—Duft, Graziano & Forest, P.C.

[57] ABSTRACT

A low-sensitizing wound cleanser product is provided for use in rinsing contaminants from injuries. The cleanser includes a combination of specially selected non-irritating ingredients that include a water and aloe vera carrier portion, an emollient portion, a hydroxyquinoline antimicrobial portion, a surfactant portion, and a preservative portion.

13 Claims, No Drawings

WOUND CLEANSER METHOD OF USE

BACKGROUND OF THE INVENTION

1. Field of the Invention

The present invention pertains to the field of wound care products and, more particularly, to washes or rinses that are used to cleanse wounds. Still more specifically, the cleanser includes a carrier portion, an emollient portion, a humectant portion, and a cosmetic biocide portion.

2. Description of the Prior Art

Superficial skin injury and skin tears may result in painful and unpleasant lesions that may progress to infection, continued wound deterioration and wound chronicity. Infections are known to be associated with rapid wound deterioration. Exposed, desiccated, and injured tissue may be slow or recalcitrant to healing, particularly in the elderly or medically compromised population.

Wound complications frequently arise in bedridden, medically compromised and institutionalized persons. Healing is frequently delayed and complicated by medical problems, the patient's low-level ambulatory status, and the availability of efficacious treatment modalities. In bedridden and institutionalized persons, tissue damage commonly induces a painful lesion that rapidly desiccates or becomes infected. Factors that may delay healing include, but are not limited to the following items: (1) poor circulation; (2) decreased elastin and collagen production in the skin (i.e., decreased cellular activity associated with healing); (3) bacterial contamination; (4) medications; and (5) extrinsic environmental factors (e.g., shear, pressure, and incontinence).

Common treatment modalities can include the application of an antibacterial wash to the wound site. This wash can be extremely irritating and/or painful to the surrounding tissue.

The U.S. Food and Drug Administration has approved guidelines for the use of cosmetic chemicals that are commonly provided in over-the-counter ointments. These chemicals are submitted to the FDA for over the counter drug review and approval. Approval is indicated by a final publication or report in the form of a monograph. The *Cosmetic Ingredient Review, Ingredient Publication Status* (Jun. 24, 1994) from the Cosmetic & Toiletry Foundation Association in Washington, D.C. provides a list of approved cosmetic chemicals. This publication provides a list of approved cosmetic ingredients, the approved functions for these ingredients, and citations to the corresponding monograph publications for each ingredient. These "cosmetic" ingredients that can be used in wound-care products, as well as other products such as lotion, hair dye and the like. The general nature and function is known for each ingredient, but great variations in efficacy can be observed based upon the precise selection of ingredients and the concentration of ingredients. Even within the approved concentration ranges, many of these approved chemicals are known to induce adverse reactions in sensitive patients.

U.S. Pat. No. 5,266,318, issued to Taylor-McCord, teaches the use of an anthraquinone-free cold processed fresh aloe vera extract for treatment of wounds to the skin. Aloe vera gel is described as a mucilaginous jelly from the parenchymal cells of the aloe plant. This jelly includes about 98.5% water with about 60% of the total solid being made up of polysaccharides, and the balance including organic acids and inorganic compounds. It is noted that a present controversy exists over the precise curative agent that is found in aloe vera, but the gel is generally acknowledged to have an ability to reduce swelling and irritation. This therapeutic benefit may be partially offset by cytotoxic activity of the yellow sap and aloin portions of the gel.

U.S. Pat. No. 5,110,593, issued to Benford, describes a topical ointment for use in treating diaper dermatitis. An antimicrobial agent consisting of 0.22% 8-hydroxyquinoline is combined with petrolatum, lanolin, beeswax, sodium borate, lanolin alcohols, methyl salicylate, sorbitan sesquioliate, methylparaben, propylparaben, and trisodium HESTA. This gel-like substance will not function as a rinse.

There remains a need for a non-irritating wound cleanser.

SUMMARY OF THE INVENTION

The present invention overcomes the problems that are outlined above by providing a non-sensitizing over the counter topical wound cleanser having specially selected non-sensitizing ingredients. The ingredients combine to provide emollient, humectant, and surfactant functions that mutually facilitate cleansing and bodily healing processes.

Broadly speaking, the non-irritating wound cleanser includes a carrier portion including water and aloe vera gel, an emollient portion, a humectant portion, a surfactant portion, a cosmetic biocide portion including oxyquinoline, and an essentially non-irritating preservative portion including at least one alkyl paraben and sodium EDTA.

The carrier portion preferably has a weight ranging from about 70% to 90% of the total weight of the cleanser. More preferably, the carrier portion includes from 65% to 75% water and from 7% to 13% aloe vera gel, determined as percentages of the total cleanser weight. The most preferred carrier includes 70% water and 10% aloe vera gel. Alternatively, the carrier may exclude aloe vera gel and consist of water.

The emollient portion serves to moisturize tissues at the wound site. This portion preferably has a weight up to about 10% of the total cleanser weight. More preferably, the emollient is an alkyl stearate in a weight ranging from 3% to 8% of the total weight. The most preferred emollient portion includes 5% butyl stearate. Other useful stearate emollients include cetyl, isobutyl, isocetyl, isopropyl, myristal, and octyl stearates. Alkyl stearates are particularly preferred because they function as surfactants, in addition to their emollient functions. Other emollients include lanolin or lanolin oil, octyl palmitate, and isopropyl lanolate.

The humectant portion serves to stabilize the moisture content of the wound site. This portion preferably has a weight up to about 10% of the total cleanser weight. More preferably, the humectant portion is glycerine in a weight ranging from 3% to 8% of the total weight. The most preferred humectant is 5% glycerine.

The surfactant portion acts as a wetting agent to increase the efficacy of the carrier in rinsing debris (e.g., dirt and grease) from the wound site area. This portion preferably has a weight up to about 10% of the total cleanser weight. More preferably, the surfactant portion is cocamphoacetate in a weight ranging from 3% to 8% of the total cleanser weight. The most preferred surfactant is 5% cocamphoacetate.

The preservative portion preferably has a weight up to 1.5% of the total cleanser weight, and is utilized to prevent microbial growth during storage. More preferably, the preservative weight includes from 0.08% to 0.12% disodium EDTA, and from 0.7% to 1.2% of at least one alkyl paraben (e.g., methyl, ethyl, propyl, and butyl), determined as percentages of the total cleanser weight. The most preferred preservative portion is formed 0.10 disodium ethylenediaminetetraacetic acid ("EDTA") and 1% methyl paraben.

The cosmetic biocide portion preferably includes oxyquinoline in an amount up to two percent by weight.

The preferred ranges of ingredients will typically yield a cleanser product having a slightly acidic pH ranging from 6.5 to 6.8. In the event that the pH falls outside of this range, a compatible pH adjusting agent should be added in an effective amount for adjusting the pH to a value within the range. Where the pH is too acidic, an alkalizer such as sodium borate may be added in amounts up to about 2% of the cleanser weight. Alternatively, a compatible acid and conjugate base buffering system may be used to control the pH.

The addition of vitamin E will assist reepithelialization of the wound site. The preferred amount of vitamin E is up to about 1% of the total cleanser weight.

A viscosifier, preferably, up to 5% cocamide DEA, may be added to thicken the cleanser and provide enhanced cleansing action. The most preferred viscosifier is 3% cocamide DEA.

DETAILED DESCRIPTION OF THE PREFERRED EMBODIMENT

Clinical experience has confirmed that substantial improvements in the efficacy of wound-care products can be obtained by: (1) preventing desiccation of the wound site; (2) reducing microbial action at the wound site; (3) eliminating nonviable cells and waste products from the wound site; (4) reducing the need for physical debridement of the wound site; and (5) reducing or eliminating sensitizing agents in wound care products that cause inflammation or other irritation. Treatment methodology following these points can greatly expedite the healing of skin-tear injuries. Nevertheless, no one single commercial product exists that performs all of these functions. The present invention presents a combination of ingredients that facilitate the above-described multifaceted treatment.

The wound cleanser has ingredients that can be divided into a number of functional groups which compliment one another to assist bodily healing processes. The combined ingredients provide a surfactant function that assists cleansing of the wound area, a humectant function that stabilizes moisture at the wound site, an emollient function that softens or soothes dried skin, a cosmetic biocide function that reduces microbial action at the wound site, an enzymatic assist function that promotes tissue regrowth, and a pH control function that provides an optimal environment for regrowth. The content of sensitizing-agents is either minimized or eliminated. Accordingly, patient discomfort is minimized while the multifunctional medicament works to expedite the healing process.

A significant percentage of patients have adverse reactions (e.g., discomfort and poor rapidity of reepithelialization) to sensitizing agents. Sensitizing agents are hereby defined as those that induce chemical burns or allergic reactions in at least some persons. Common sensitizing agents, e.g., dexpanthenol, chlorides, chamomile, propylene glycol, and lanolin alcohols, are preferably avoided. Substantial improvements in wound-care efficacy may be observed in wound-care products having reduced contents of these sensitizing agents. The ingredients of the present medicament, accordingly, minimize the content of sensitizing agents. In contrast, prior practices have been to include such chemicals in small amounts for their perceived benefits.

Reepithelialization occurs most effectively in an environment having a slightly acidic pH, i.e., one ranging from about 6.5 to 6.8. This environment simultaneously fosters the migration and growth of new epithelial cells while inhibiting bacterial growth. Without pH adjustment, the preferred ranges of ingredients will typically have a pH below 6.5. Accordingly, it is preferred to adjust the pH by adding a compatible alkalizer in an effective amount for obtaining a pH value within the preferred range. Particularly preferred alkalizers include triethanolamine at a concentration of up to about 1% (w/w) or sodium borate at a concentration of up to about 1% (w/w). Alternatively, a compatible acid and conjugate base buffer system may be utilized to hold the pH at slightly acidic values.

The following non-limiting example sets forth preferred materials and methods for practicing the present invention.

EXAMPLE 1

WOUND CLEANSER

The ingredients listed in Table 1 below can be acquired from commercial sources and mixed in the weight percentages indicated to provide a spray-on liquid composition. The ingredients are vigorously mixed to form a liquid solution.

TABLE 1

| Cleanser Portion | Ingredient | Weight (%) |
|---|---|---|
| Carrier | Deionized Water | 70.13 |
| | Aloe Vera Gel | 10.00 |
| *** | Carrier Subtotal | *80.13 |
| Humectant | Glycerine 96% | *5.00 |
| Emollient | Butyl Stearate | *5.00 |
| Cosmetic biocide | Hydroxyquinoline | *0.72 |
| Preservative | Disodium EDTA | 0.10 |
| | Methylparaben | 1.00 |
| *** | Preservative Subtotal | *1.10 |
| Surfactant | Cocamphoacetate | *5.00 |
| Viscosifier | Cocamide DEA | *3.00 |
| Vitamin E | α-tocopherol | *0.05 |
| | Total | 100.00 |

The resultant cleanser is a low to medium viscosity liquid solution having a pH of about 6.5. The liquid can be applied to a wound site through the use of a conventional spray bottle apparatus. The application of spray liquid permits a complete flushing of the wound site to soften and rinse away debris from the wound, thereby minimizing the need for physical scrubbing. Cleansing is performed as needed, and is suggested three to four times per day with the frequency of application decreasing as the wound heals. The viscosity of the cleanser is low enough to permit spray application.

Those skilled in the art will understand that the preferred embodiments described above may be subjected to obvious modifications without departing from the true scope and spirit of the invention. Accordingly, the inventors hereby state their intention to rely upon the Doctrine of Equivalents to protect their full rights in the invention.

I claim:

1. A non-irritating cleanser mixture for use in rinsing wounds, consisting essentially of:

a carrier portion including water and aloe vera gel, said carrier portion having a weight ranging from about 70% to 90% of a total weight of said cleanser;

an emollient portion having a weight ranging from 3% to 8% of said total weight;

a humectant portion having a weight ranging from 3% to 8% of said total weight;

a surfactant portion having a weight ranging from 3% to 8% of said total weight;

a cosmetic biocide portion including oxyquinoline in an effective amount for reducing microbial action at the wound site; and an essentially non-irritating preservative portion including at least one alkyl paraben and sodium EDTA.

2. The cleanser as set forth in claim 1, said carrier portion consisting of from 65% to 75% (w/w) water and from 7% to 13% (w/w) aloe vera gel.

3. The cleanser as set forth in claim 1, said emollient portion consisting of butyl stearate.

4. The cleanser as set forth in claim 1, said humectant portion consisting of glycerine.

5. The cleanser as set forth in claim 1, said surfactant portion consisting of cocamphoacetate.

6. The cleanser as set forth in claim 1, said preservative portion consisting of from 0.08% to 0.12% (w/w) disodium EDTA and from 0.5% to 1.5% (w/w) alkyl paraben.

7. The cleanser as set forth in claim 1, said cleanser having a pH ranging from about 6.5 to 6.8.

8. The cleanser as set forth in claim 7, additionally consisting essentially of a pH adjusting agent in an effective amount for adjusting a pH of said cleanser within a range from 6.5 to 6.8.

9. The cleanser as set forth in claim 8, said pH adjusting agent including sodium borate in an amount up to about 2% of said total weight.

10. The cleanser as set forth in claim 1, said cleanser being essentially free of sensitizing agents including dexpanthenol, chlorides, chamomile, and propylene glycol.

11. The cleanser as set forth in claim 1 additionally consisting essentially of up to 1% vitamin E.

12. A method of rinsing wounds comprising the steps of:
providing the non-irritating cleanser mixture according to claim 1; and rinsing a wound with said non-irritating cleanser mixture.

13. The method as set forth in claim 12, wherein said rinsing step includes a step of spraying said non-irritating cleanser mixture onto said wound.

* * * * *